(12) United States Patent
Kano et al.

(10) Patent No.: US 11,484,357 B2
(45) Date of Patent: Nov. 1, 2022

(54) HIGH FREQUENCY TREATMENT INSTRUMENT

(71) Applicant: Olympus Corporation, Hachioji (JP)

(72) Inventors: Akihito Kano, Tachikawa (JP); Mizuki Komiya, Hachioji (JP); Ryuhei Shimada, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 853 days.

(21) Appl. No.: 16/195,080

(22) Filed: Nov. 19, 2018

(65) Prior Publication Data

US 2019/0117293 A1    Apr. 25, 2019

Related U.S. Application Data

(63) Continuation of application No. PCT/JP2016/065484, filed on May 25, 2016.

(51) Int. Cl.
*A61B 18/14* (2006.01)
*A61B 18/00* (2006.01)
(Continued)

(52) U.S. Cl.
CPC .. *A61B 18/1445* (2013.01); *A61B 2017/2925* (2013.01); *A61B 2017/320094* (2017.08);
(Continued)

(58) Field of Classification Search
CPC .... A61B 18/1445; A61B 2017/320094; A61B 2018/00994; A61B 2218/002; A61B 2018/00589
See application file for complete search history.

(56) References Cited

U.S. PATENT DOCUMENTS

2005/0033278 A1* 2/2005 McClurken ........ A61B 18/1445
606/41
2007/0049920 A1 3/2007 McClurken et al.
(Continued)

FOREIGN PATENT DOCUMENTS

JP    2010-517597    5/2010
JP    2010-517598    5/2010
(Continued)

OTHER PUBLICATIONS

International Search Report and Written Opinion from corresponding International Application No. PCT/JP2016/065484, dated Aug. 23, 2016.
(Continued)

*Primary Examiner* — Linda C Dvorak
*Assistant Examiner* — Ryan T Clark
(74) *Attorney, Agent, or Firm* — Oliff PLC

(57) ABSTRACT

A high frequency treatment instrument can be opened and closed between a first grasping jaw and a second grasping jaw. A lumen is formed inside the first grasping jaw. The first grasping jaw includes an electrode disposed on a side toward which the first gasping jaw is closed, with respect to the lumen. The electrode has an electrode surface arranged opposite the second grasping jaw and extending from a proximal end portion to a distal end portion of the first grasping jaw. The first grasping jaw has a distal end wall disposed opposing from a distal end side of the first grasping jaw toward a distal end edge of the electrode surface, and a clearance between the distal end edge of the electrode surface and the distal end wall communicates to the lumen and opens toward the side toward which the first grasping jaw is closed.

15 Claims, 5 Drawing Sheets

(51) Int. Cl.
  *A61B 17/32* (2006.01)
  *A61B 17/29* (2006.01)
(52) U.S. Cl.
  CPC .............. *A61B 2018/00029* (2013.01); *A61B 2018/00404* (2013.01); *A61B 2018/00529* (2013.01); *A61B 2018/00589* (2013.01); *A61B 2018/00994* (2013.01); *A61B 2218/002* (2013.01)

(56) References Cited

U.S. PATENT DOCUMENTS

| | | | |
|---|---|---|---|
| 2008/0195090 A1 | 8/2008 | Takashino et al. | |
| 2008/0195091 A1 | 8/2008 | Takashino et al. | |
| 2010/0057081 A1 | 3/2010 | Hanna | |
| 2011/0306968 A1* | 12/2011 | Beckman | A61B 18/1482 606/41 |
| 2012/0101493 A1 | 4/2012 | Masuda et al. | |
| 2013/0345702 A1 | 12/2013 | Wandel | |
| 2014/0194868 A1 | 7/2014 | Sanai et al. | |
| 2017/0105790 A1* | 4/2017 | Onuma | A61B 18/12 |

FOREIGN PATENT DOCUMENTS

| | | |
|---|---|---|
| JP | 2014-004365 | 1/2014 |
| WO | 2004026104 | 4/2004 |
| WO | 2008099529 | 8/2008 |
| WO | 2008099530 | 8/2008 |
| WO | 2011089769 | 7/2011 |
| WO | 2013157571 | 10/2013 |

OTHER PUBLICATIONS

Office Action from corresponding Japanese Application No. 2017-544983.

* cited by examiner

HIGH FREQUENCY TREATMENT INSTRUMENT

CROSS-REFERENCE TO RELATED APPLICATION

This application is a continuation application of PCT Application No. PCT/JP2016/065484 filed on May 25, 2016, which is hereby incorporated by reference in its entirety.

TECHNICAL FIELD

The disclosed technology generally relates to a high frequency treatment instrument, which treats a treatment object by applying a high frequency electric current to the treatment object.

DESCRIPTION OF THE RELATED ART

US 2007/0049920 A1 discloses a high frequency treatment instrument for performing treatment of proteins in a treatment object such as biological tissue by grasping the treatment object between a pair of grasping jaws and causing a high frequency electric current to flow through the treatment object grasped between the grasping jaws. In the treatment with a high frequency electric current, a treatment object may be heated to high temperature. In this case, there is a possibility that the treatment object may stick on the grasping jaws or may undergo char formation.

There is a need for a high frequency treatment instrument which effectively prevents sticking, char formation or the like of a treatment object and efficiently applies a high frequency electric current to the treatment object.

BRIEF SUMMARY OF EMBODIMENTS

One aspect of the disclosed technology is directed to a high frequency treatment instrument comprises a first grasping jaw having opposed respective proximal and distal end portions. The first grasping jaw includes a lumen formed therein that extends from the proximal end portion to the distal end portion. A second grasping jaw is configured to be engaged with the first grasping jaw so as to relatively pivot with respect to one another. The first grasping jaw includes an electrode coupled and extends over from the proximal end portion to the distal end portion of the first grasping jaw. The electrode is positioned to face against the second grasping jaw when the first grasping jaw and the second grasping jaw are in a closed position with respect to one another. The electrode has a distal end edge adjacent the distal end portion. The first grasping jaw forms a first clearance defined by a distal end wall positioned opposite the distal end edge of the electrode. The first clearance is in fluid communication with the lumen. The first grasping jaw includes a fluid port being connected to a fluid feed line to transfer fluid to the lumen.

Another aspect of the disclosed technology is directed to a method of using a high frequency treatment instrument for treating liver parenchyma or a liver blood vessel. The method comprises the steps of grasping the liver parenchyma or liver blood vessel by respective first and second grasping jaws simultaneously in an abdominal cavity, causing a high frequency electric current to flow across an electrode. The electrode that is disposed between the respective first and second grasping jaws applies the high frequency electric current to the liver parenchyma or liver blood vessel. Next, directing a fluid into a lumen disposed in the first grasping jaw, before or during the application of the high frequency electric current to the liver parenchyma or liver blood vessel. And then, removing the fluid out from a clearance formed between a distal end edge of the electrode and a distal end wall disposed opposite the distal end edge of the electrode on the first grasping jaw.

A further aspect of the disclosed technology is directed to a treatment system comprises an energy control system. A high frequency treatment instrument is configured to be coupled to the energy control system so as to apply a high frequency electric current to a body tissue without sticking and/or char formation thereto. The high frequency treatment instrument comprises a housing having a handle attached thereto. A sheath has respective proximal and distal ends. The sheath is attached to the housing via the proximal end. An end effector is configured to be attached to the sheath via the distal end. The end effector includes respective first and second grasping jaws each of which is pivotally attached to the sheath. The first grasping jaw and/or second grasping jaw are capable of grasping the body tissue via the handle. The first grasping jaw includes an electrode being disposed in an inner side of the first grasping jaw to form a lumen therebetween. The lumen receives fluid from a fluid feed line so as to cool off the respective first and second grasping jaws during an operation and preventing char formation or sticking of the body tissue to the respective first and second grasping jaws. The first grasping jaw includes a recess formed in the inner side thereof to contain the electrode therein. The sheath includes a moveable member disposed therein and connected to the handle so as to permit the respective first and second grasping jaws pivoting with respect to one another. The first grasping jaw includes a support member formed thereon and being used to support the electrode rockably. At least one of the first grasping jaw and the second grasping jaw includes a heating element that generates heat.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

First Embodiment

Referring to FIGS. 1 through 4, a description will be made about a first embodiment of the present disclosure.

Figure 1:
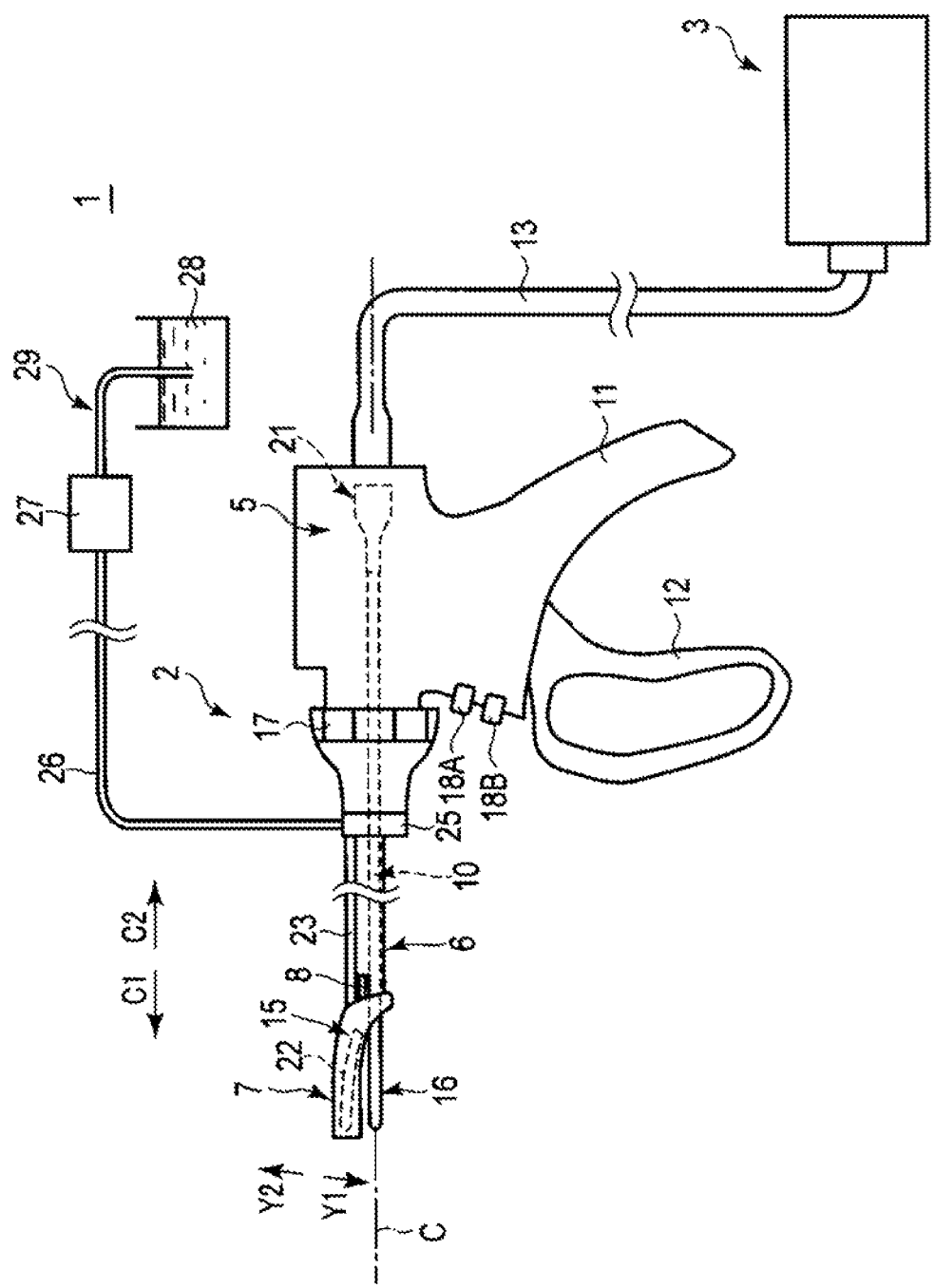
FIG. 1 is a schematic view illustrating a treatment system according to a first embodiment.

FIG. 1 is a view illustrating a treatment system 1 according to this embodiment. As illustrated in FIG. 1, the treatment system 1 includes a high frequency treatment instrument 2 and an energy control system 3. The high frequency treatment instrument 2 has a longitudinal axis C. Here, a side in a direction along the longitudinal axis C is assumed to be a distal end side or the side indicated by an arrow C1, while a side opposite to the distal end side is assumed to be a proximal end side or the side indicated by an arrow C2.

The high frequency treatment instrument 2 also includes a hand-holdable housing 5, a shaft or sheath 6 connected to a distal end side of the housing 5, and an end effector 7 disposed on a distal end portion of the shaft 6. The shaft 6 is disposed centering substantially around the longitudinal axis C and extending along the longitudinal axis C. On the housing 5, a grip or a fixed handle 11 is arranged, and a handle or a movable handle 12 is pivotally attached. The handle 12 is pivoted relative to the housing 5, whereby the handle 12 is opened or closed with respect to the grip 11.

The end effector 7 includes a first grasping jaw 15 and a second grasping jaw 16. The first grasping jaw 15 is pivotally attached to the distal end portion of the shaft 6. Inside the shaft 6, a movable member 8 is disposed extending along the longitudinal axis C. Inside the housing 5, the movable member 8 is connected to the handle 12. Also, the movable member 8 is connected at a distal end portion thereof to the first grasping jaw 15. By opening or closing the handle 12 with respect to the grip 11, the movable member 8 is driven so that the movable member 8 is allowed to move relative to the housing 5 and the shaft 6 along the longitudinal axis C. As a consequence, the first grasping jaw 15 pivots about the position of its attachment to the shaft 6, so that the first grasping jaw 15 is opened or is closed with respect to the second grasping jaw 16. Accordingly, the paired grasping jaws 15 and 16 open or close. By closing the paired grasping jaws 15 and 16, a treatment object such as biological tissue can be grasped between the grasping jaws 15 and 16. The open/close direction of the first grasping jaw 15, in other words, the direction indicated by an arrow Y1 and an arrow Y2 intersects the longitudinal axis C, in other words, is substantially perpendicular to the longitudinal axis C.

The second grasping jaw 16 may be integral with the shaft 6 or may be fixed to the shaft 16, or may be pivotally attached to the shaft 6. In a case in which the second grasping jaw 16 is pivotally attached to the shaft 6, the movable member 8 is moved along the longitudinal axis C, whereby the second grasping jaw 16 in addition to the first grasping jaw 15 is also pivoted relative to the shaft 6 and the grasping jaws 15 and 16 hence open or close. Also, in certain examples, a rod member which is, for example, designated at numeral reference 10 may be disposed, specifically inserted through the shaft 6, and the second grasping jaw 16 may be formed by a portion of the rod member 10, the portion protruding from the shaft 6 toward the distal end side. Moreover, in this embodiment, a turnable knob 17 is attached to the housing 5. By turning the turnable knob 17 relative to the housing 5, the shaft 6, the end effector 7, and the movable member 8 are turned together with the turnable knob 17 about the longitudinal axis C or a central axis of the shaft 6.

A cable 13 is connected at an end thereof to the housing 5. The cable 13 is connected at an opposite end thereof to the energy control system 3. To the housing 5, control buttons 18A and 18B are also attached as energy control input portions. By independently pressing the control buttons 18A and 18B, control is input to the energy control system 3 in order to output electric energy from the energy control system 3 to the high frequency treatment instrument 2. In place of or in addition to the control buttons 18A and 18B, a footswitch or the like, which is discrete from the high frequency treatment instrument 2, may be included as an energy control input portion.

The energy control system 3 includes a power source such as a battery or a power outlet, a conversion circuit, a control unit such as a processor or an integrated circuit, and a storage medium. The conversion circuit converts electric power from the power source to electric energy to be supplied to the high frequency treatment instrument. The control unit includes a central processing unit (CPU), an application specific integrated circuit (ASIC), or the like. Based on a control input through the control button 18A or the energy control input portion, the energy control system 3 outputs high frequency electric energy as electric energy. The high frequency electric energy output from the energy control system 3 is supplied to the first grasping jaw 15 and the second grasping jaw 16.

In certain examples, the second grasping jaw 16 is formed by the portion of the rod member 10 described hereinbefore, the portion protruding from the shaft 6, and inside the housing 5, an ultrasonic transducer 21 is connected to a proximal end side of the rod member 10. When a control input is performed through the control button 18B, high frequency electric energy is supplied to the grasping jaws 15 and 16 from the energy control system 3, and at the same time, electric energy different from the high frequency electric energy supplied to the grasping jaws 15 and 16, for example, AC power of a predetermined frequency is supplied from the energy control system 3 to the ultrasonic transducer 21. As a consequence, ultrasonic vibrations occur at the ultrasonic transducer 21. The ultrasonic vibrations occurred at the ultrasonic transducer 21 are transmitted to the second grasping jaw 16 by way of the rod member 10. Consequently, the rod member 10 including the second grasping jaw 16 is caused to resonate or vibrate, whereby ultrasonic vibrations are applied as treatment energy to the treatment object grasped between the grasping jaws 15 and 16.

In some different examples, a heating element 22 may be disposed in at least one of the grasping jaws 15 and 16, for example, the first grasping jaw 15. When a control input is performed through the control button 18B, high frequency electric energy is supplied to the grasping jaws 15 and 16 from the energy control system 3, and at the same time, electric energy different from the high frequency electric energy supplied to the grasping jaws 15 and 16, for example, DC electric power or AC electric power is supplied from the energy control system 3 to the heating element 22. As a consequence, heat is generated at the heating element 22, and the generated heat is applied as treatment energy to the grasped treatment object.

On an outer peripheral surface of the shaft 6, a feed tube 23, or a fluid feed line 23, is disposed extending along the longitudinal axis C. The feed tube 23 is connected at an end thereof, specifically a distal end thereof to the first grasping jaw 15. On a distal end side of the turnable knob 17, a coupler member 25 is fixed. The feed tube 23 is connected at an opposite end thereof, specifically a proximal end thereof to the fluid coupler 25. The feed tube 23 and coupler member 25 are turnable together with the turnable knob 17 and the shaft 6 relative to the housing 5 about the longitudinal axis C.

An external tube 26 is connected at an end thereof to the coupler member 25. In the coupler member 25, the feed tube 23 and the external tube 26 internally communicate to each other. The external tube 26 is connected at an opposite end thereof to a liquid source 29 that includes a feed pump 27 and a liquid tank 28. When the feed pump 27 is driven, a liquid such as physiological saline stored in the liquid tank 28 is supplied through the inside of the external tube 26. Along a feed route inside the feed tube 23, the liquid is then supplied or fed from the proximal end side to the distal end side. In certain examples, the feed tube 23 may be disposed extending along the longitudinal axis C inside the shaft 6, and the liquid may be supplied from the proximal end side toward the distal end side through the feed route inside the feed tube 23. In some different examples, a multi-lumen tube, not illustrated, may be disposed extending along the longitudinal axis C. In such a case, the shaft 6 is inserted through one of lumens in the multi-lumen tube, and another lumen is used as a feed route supplying the liquid from the proximal end side to the distal end side.

Figure 2:
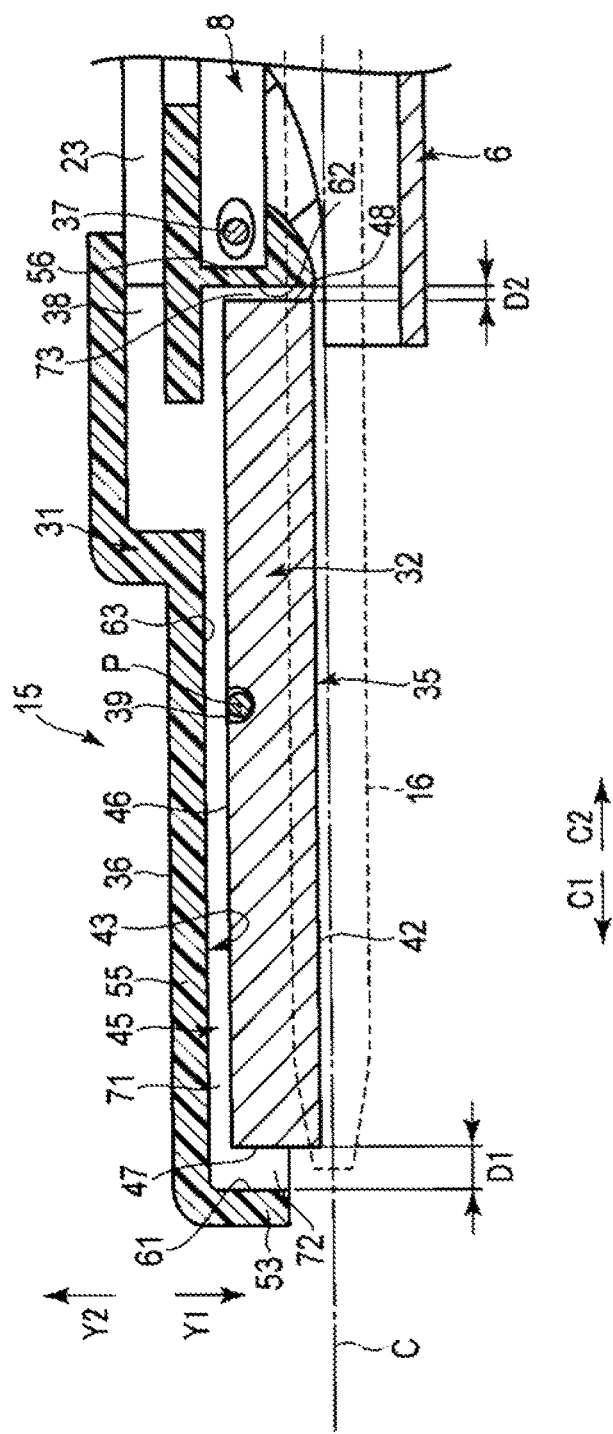
FIG. 2 is a cross-sectional view schematically depicting a first grasping jaw in the first embodiment in a cross-section substantially perpendicular to a width direction.
Figure 3:
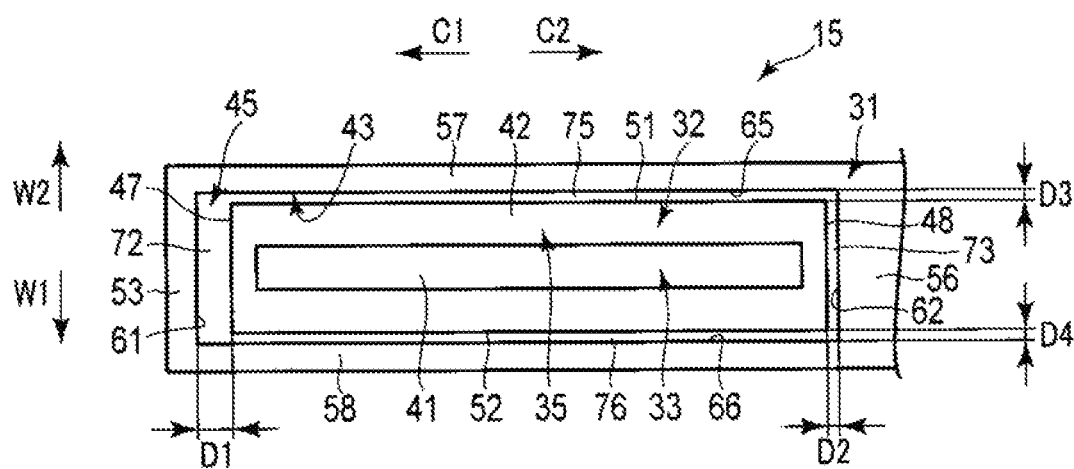
FIG. 3 is a schematic view of the first grasping jaw in the first embodiment as seen from a side toward which the first grasping jaw is closed, in other words, from a side of a grasping surface.
Figure 4:
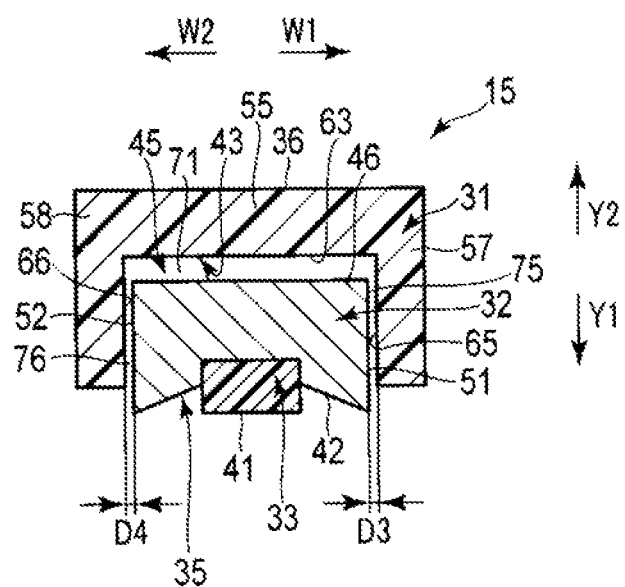
FIG. 4 is a cross-sectional view schematically depicting the first grasping jaw in the first embodiment in a cross-section substantially perpendicular to a direction along a longitudinal axis.

FIGS. 2 to 4 depict the configuration of the first grasping jaw 15. Here, a direction, which intersects at substantially right angles the longitudinal axis C, in other words, the direction of extending disposition of the first grasping jaw 15 and also intersects, in other words, is substantially perpendicular to the open/close direction of the first grasping jaw 15, in other words, directions indicated by the arrow Y1 and the arrow Y2, is assumed to be a width direction of the first grasping jaw 15 or the end effector 7, that is, a direction indicated by an arrow W1 and an arrow W2. FIG. 2 depicts the first grasping jaw 15 in a cross-section substantially perpendicular to the width direction. FIG. 3 depicts the first grasping jaw 15 as seen from a side toward which the first grasping jaw is closed, in other words, a side indicated by arrow Y1. FIG. 4 depicts the first grasping jaw 15 in cross-section substantially perpendicular to the direction along the longitudinal direction C.

As depicted in FIGS. 2 to 4, the first grasping jaw 15 has a proximal end and a distal end, and is disposed extending from the proximal end to the distal end along the longitudinal axis C. The first grasping jaw 15 includes a support member 31, an electrode 32, and a pad member 33. The support member 31, the electrode 32, and the pad member 33 are disposed extending over from a proximal end portion to a distal end portion of the first grasping jaw 15. The electrode 32 is formed from an electrically conductive material, while the pad member 33 is formed from an electrically insulating material. Preferably, the support member 31 may have coating applied to a surface thereof with an electrically insulating material.

In this embodiment, by the electrode 32 and the pad member 33, a grasping surface 35 is formed on the outer front surface of the first grasping jaw 15 such that the grasping surface 35 faces a side toward which the first grasping jaw 15 is closed, in other words, the side indicated by the arrow Y1, and by the support member 31, a back surface 36 is formed on the outer front surface of the first grasping jaw 15 such that the back surface 36 faces a side toward which the first grasping jaw 15 is opened, in other words, the side indicated by the arrow Y2. The grasping surface 35 opposes the second grasping jaw 16, so that the treatment object grasped between the grasping jaws 15 and 16 comes in contact with the grasping surface 35.

The support member 31 is pivotally attached to the shaft 6, and is connected to a distal end portion of the movable member 8 via a connecting pin 37. Therefore, the position of attachment of the support member 31 to the shaft 6 serves as a fulcrum for pivotal motion of the support member 31, in other words, the first grasping jaw 15, and the position of connection of the support member 31 to the movable member 8 serves as a point of effort where drive force is applied to cause pivoting of the support member 31. A port 38, or a fluid port, is formed in the support member 31 of the first grasping jaw 15. In the port 38, the feed tube 23 is connected at an end thereof, specifically the distal end thereof to the support member 31 from the proximal end side, so that the port 38 communicates with the feed route inside the feed tube 23. In the examples in which the feed route is formed by one of the lumens in the multi-lumen tube, the port 38 communicates to the lumen of the multi-lumen tube, which is used as the feed route.

The electrode 32 is secured to the support member 31 via a connecting pin 39. Further, the pad member 33 is fixed on the electrode 32. The electrode 32 and pad member 33 are rockable about a pivot axis P relative to the support member 31. In other words, the support member 31 rockably supports the electrode 32. In this embodiment, the pivot pin P is substantially coaxial with a central axis of the connecting pin 39, and extends substantially in parallel to the width direction of the first grasping jaw 15. The pad member 33 includes a contact surface 41, which can be bought into contact with the second grasping jaw 16 when the first grasping jaw 15 is closed relative to the second grasping jaw 16. The contact surface 41 forms a part of the grasping surface 35. On the other hand, the electrode 32 includes an electrode surface 42, or an opposing electrode surface, which opposes the second grasping jaw 16, and the electrode surface 42 forms parts of the grasping surface 35. With the contact surface 41 of the pad member 33 being in contact with the second grasping jaw 16, the electrode 32 including the electrode surface 42 has a clearance relative to the second grasping jaw 16, in other words, is apart from the second grasping jaw 16. The contact surface 41 and electrode surface 42 are arranged extending continuously from the proximal end portion to the distal end portion in the first grasping jaw 15.

When high frequency electric energy is supplied to the grasping jaws 15 and 16 from the energy control system 3, different potentials occur at the electrode 32 in the first grasping jaw 15 and at the second grasping jaw 16, respectively. Therefore, a high frequency electric current flows through the treatment object between the electrode 32, or the electrode surface 42, and the second grasping jaw 16 when the high frequency electric energy is supplied to the grasping jaws 15 and 16 with the grasped treatment target being in contact with the electrode 32 and the second grasping jaw 16. As a consequence, the high frequency electric current is applied as treatment energy to the treatment target grasped between the grasping jaws 15 and 16.

The support member 31 in the first grasping jaw 15 includes a recessed surface 43 recessed toward the side toward which the first grasping jaw 15 is opened, in other words, toward the back surface 36. The recessed surface 43 forms a recess 45 or a space, in which the electrode 32 and pad member 33 are inserted. The electrode 32 includes in a surface thereof the above-mentioned electrode surface 42 or the opposing electrode surface, a back electrode surface 46 facing a side toward which the first grasping jaw 15 is opened, in other words, an opposite side to the electrode surface 42, a distal end electrode edge 47, or a distal end electrode surface, facing the distal end side (the side indicated by arrow C1), and a proximal end electrode edge 48, or a proximal end electrode surface, facing the proximal end side (the side indicated by arrow C2). The distal end electrode edge 47, or the distal end electrode surface, is arranged in the distal end portion of the first grasping jaw 15, and the proximal end electrode edge 48, or the proximal end electrode surface, is arranged in the proximal end portion of the first grasping jaw 15. The surface of the electrode 32 also includes a first side electrode surface 51, or a first side electrode edge, facing one of opposite sides in the width direction of the first grasping jaw 15, in other words, the side indicated by arrow W1, and a second side electrode surface 52, or a second side electrode edge, facing the other side in the width direction of the first grasping jaw 15, in other words, the side indicated by arrow W2.

The support member 31 includes a distal end wall 53 covering the electrode 32 from the distal end side, a back wall 55 covering the electrode 32 from the side toward which the first grasping jaw 15 is opened, in other words, the side of the back surface 36, and a proximal end wall 56 covering the electrode 32 from the proximal end side. The distal end wall 53 is disposed on the distal end side of the electrode 32, and opposes the distal end electrode edge 47 of the electrode 32. The support member 31 also includes a first side wall 57 covering the electrode 32 from the one side in the width direction of the first grasping jaw 15, and a second side wall 58 covering the electrode 32 from the other side in the width direction of the first grasping jaw 15. The electrode 32 is, therefore, covered by the side walls 57 and 58 from an outside in the width direction of the first grasping jaw 15.

The recessed surface 43 includes a recessed distal end surface 61 formed from the distal end wall 53 and a recessed proximal end surface 62 formed from the proximal end wall 56. The recessed distal end surface 61 forms a distal end of the recessed surface 43, while the recessed proximal end surface 62 forms a proximal end of the recessed surface 43. The recessed distal end surface 61 is located on the distal end side relative to the distal end electrode edge 47, and opposes the distal end electrode edge 47. On the other hand, the recessed proximal end surface 62 is located on the proximal end side relative to the proximal end electrode edge 48, and opposes the proximal end electrode edge 48.

The recessed surface 43 includes a recessed bottom surface 63 formed from the back wall 55. The recessed bottom surface 63 is located on the side toward which the first grasping jaw 15 is opened, in other words, the side of the back surface 36, with respect to the back surface 36, and opposes the back electrode surface 46. The recessed surface 43 also includes a first recessed side surface 65 formed from the first side wall 57 and a second recessed side surface 66 formed from the second side wall 58. The first recessed side surface 65 is located on the one side in the width direction of the first grasping jaw 15, in other words, the side indicated by arrow W1, relative to the first side electrode surface 51, and opposes the first side electrode surface 51. The second recessed side surface 66 is located on the other side in the width direction of the first grasping jaw 15, in other words, the side indicated by arrow W2, relative to the second side electrode surface 52, and opposes the second side electrode surface 52.

Between the back electrode surface 46 of the electrode 32 and the recessed bottom surface 63 of the recessed surface 43, in other words, the back wall 55 of the support member 31, a lumen 71 is formed by the recess 45, or the space. The lumen 71 is disposed extending toward the distal end portion of the first grasping jaw 15 from the proximal end side toward the distal end side inside the first grasping jaw 15. The electrode 32 is disposed on the side toward which the first grasping jaw 15 is closed, in other words, toward the grasping surface 35, with respect to the lumen 71, and the back wall 55 of the support member 31 is disposed on the side toward which the first grasping jaw 15 is opened, in other words, the side away from the grasping surface 35, with respect to the lumen 71. The lumen 71 is, therefore, more remote from the second grasping jaw 16 than the electrode 32. The lumen 71 communicates to the port 38. Accordingly, the liquid which has been supplied toward the distal end side along a feed route inside the feed tube 23 flows from the port 38 into the lumen 71. In examples in which a feed route is formed by one of lumens in a multi-lumen tube, a liquid which has been supplied through the lumen as the feed route in the multi-lumen tube flows into the lumen 71.

Between the distal end electrode edge 47, or the distal end electrode surface, of the electrode 32 and the recessed distal end surface 61 of the recessed surface 43, in other words, distal end wall 53 of the support member 31, a clearance 72 is formed by the recess 45, or the space, and between the proximal end electrode edge 48, or the proximal end electrode surface, of the electrode 32 and the recessed proximal end surface 62 of the recessed surface 43, in other words, the proximal end wall 56 of the support member 31, a clearance 73 is formed by the recess 45, or the space. The clearance 72 opens toward the side toward which the first grasping jaw 15 is closed, between the distal end electrode edge 47 of the electrode 32 and the distal end wall 53, while the clearance 73 opens toward the side toward which the first grasping jaw 15 is closed, in other words, the side of the grasping surface 35, between the proximal end electrode edge 48 of the electrode 32 and the proximal end wall 56. Further, between the first side electrode surface 51, or the first side electrode edge, of the electrode 32 and the first recessed side surface 65 of the recessed surface 43, in other words, the first side wall 57 of the support member 31, a clearance 75 is formed by the recess 45 or the space, and between the second side electrode surface 52, or the second side electrode edge, of the electrode 32 and the second recessed side surface 66 of the recessed surface 43, in other words, the second side wall 58 of the support member 31, a clearance 76 is formed by the recess 45, or the space. The clearance 75 opens toward the side toward which the first grasping jaw 15 is closed, in other words, the side of the second grasping jaw 16, between the first side electrode surface 51 of the electrode 32 and the first side wall 57, while the clearance 76 opens toward the side toward which the first grasping jaw 15 is closed, in other words, the side of the grasping surface 35, between the second side electrode surface 52 of the electrode 32 and the second side wall 58.

In the first grasping jaw 15, the clearances 72, 73, 75, and 76 communicate to the lumen 71. Therefore, the liquid which has flowed into the lumen 71 flows into each of the clearances 72, 73, 75, and 76, and flows out from openings of the respective clearances 72, 73, 75, and 76 toward the side toward which the first grasping jaw 15 is closed, in other words, the side of the second grasping jaw 16, to the outside of the first grasping jaw 15. The electrode 32 does not include any hole or the like that extends through the electrode 32 from the electrode surface 42, or the opposing electrode surface, to the back electrode surface 46. Therefore, the liquid which has flowed into the lumen 71 does not outwardly flow toward the side toward which the first grasping jaw 15 is closed, through the inside of the electrode 32. In other words, the liquid which has flowed into the lumen 71 flows toward the side toward which the first grasping jaw 15 is closed, in other words, the side of the grasping surface 35, to the outside of the first grasping jaw 15 only through the clearances 72, 73, 75, and 76 between the outer edges 47, 48, 51, and 52 of the electrode 32, or the electrode surface 42, and the recessed surface 43.

The distal end electrode edge 47 of the electrode 32 and the distal end wall 53, or the recessed distal end surface 61, are apart from each other by a distance D1, and the proximal end electrode edge 48 of the electrode 32 and the proximal end wall 56, or the recessed proximal end surface 62, are apart from each other by a distance D2. The first side electrode surface 51 of the electrode 32 and the first side wall 57, or the first recessed side surface 65, are apart from each other by a distance D3, and the second side electrode surface 52 of the electrode 32 and the second side wall 58, or the second recessed side surface 66, are apart from each other by a distance D4. Between the proximal end electrode edge 48 of the electrode 32 and the proximal end wall 56, the distance D2 is set to be 0 or small. As a consequence, flow path resistance is applied, for example, under the action of surface tension or the like in the clearance 73, so that the liquid hardly flows through the clearance 73. Similarly, the distance D3 is set to be 0 or small between the first side electrode surface 51 of the electrode 32 and the first side wall 57. As a consequence, flow path resistance is applied, for example, under the action of surface tension or the like in the clearance 75, so that the liquid hardly flows through the clearance 75. Further, the distance D4 is set to be 0 or small between the second side electrode surface 52 of the electrode 32 and the second side wall 58. As a consequence, flow path resistance is applied, for example, under the action of surface tension or the like in the clearance 76, so that the liquid hardly flows through the clearance 76. The distance D1 is set to be greater compared with each of the distances D2 to D4. Hence, the distance D1 between the distal end electrode edge 47, or the distal end electrode surface, of the electrode 32 and the distal end wall 53 is greater than any of the distances D2, D3, and D4 between the parts 48, 51, and 52, which are other than the distal end electrode edge 47 on the outer edges 47, 48, 51, and 52 of the electrode 32, or the electrode surface 42, and the recessed surface 43. Owing to the configuration as described hereinbefore, the clearance 72 has a greater flow path cross-sectional area than any of the clearances 73, 75, and 76, and therefore is smaller in flow path resistance than any of the clearances 73, 75, and 76. Therefore, the liquid which has flowed into the lumen 71 is easier to flow into the clearance 72 compared with any of the clearances 73, 75, and 76. As a consequence, a large majority of the liquid which has flowed into the lumen 71 outwardly flows from the opening of the clearance 72 toward the side toward which the first grasping jaw 15 is closed, and substantially none of the liquids flows out from the openings of the respective clearances 73, 75, and 76.

A description will next be made about functions and advantageous effects of the high frequency treatment instrument 2 in this embodiment. The treatment system 1 according to this embodiment is used, for example, in the treatment of the liver, and incision of liver parenchyma, incision of a liver blood vessel, liver hemostasis (coagulation) or the like is performed using the treatment system 1.

Upon performing the incision of liver parenchyma, the end effector 7 is inserted into the abdominal cavity, or body cavity, and the liver parenchyma as the treatment object is grasped between the paired grasping jaws 15 and 16. Here, the grasping surface 35 of the first grasping jaw 15 and a grasping surface of the second grasping jaw 16, in other words, a surface of the second grasping jaw 16, the surface opposing the first grasping jaw 15, each come into contact with the liver parenchyma, or the treatment object, over a range from the proximal end portion to the distal end portion. As a consequence, the electrode surface 42, or the opposing electrode surface, of the electrode 32 comes into contact with the liver parenchyma over substantially the entire length thereof from the proximal end portion to the distal end portion. With the liver parenchyma being grasped between the grasping jaws 15 and 16, the surgeon performs a control input through the control button 18B. When the control input has been performed through the control button 18B, high frequency electric energy is applied across the grasping jaws 15 and 16 from the energy control system 3, and at the same time, electric energy is supplied from the energy control system 3 to the ultrasonic transducer 21. Ultrasonic vibrations then occur at the ultrasonic transducer 21. The ultrasonic vibrations occurred at the ultrasonic transducer 21 are transmitted to the second grasping jaw 16. Consequently, the high frequency electric current flows through the liver parenchyma across the electrode 32 of the first grasping jaw 15 and the second grasping jaw 16, and at the same time, the liver parenchyma is incised with frictional heat generated by the ultrasonic vibrations.

Upon incising a liver blood vessel, on the other hand, the liver blood vessel is grasped between the grasping jaws 15 and 16 in the abdominal cavity. Here, the grasping surface 35 of the first grasping jaw 15 and the grasping surface of the second grasping jaw 16, in other words, the surface of the second grasping jaw 16, the surface opposing the first grasping jaw 15, each come into contact with the blood vessel at a central part thereof in a direction along the longitudinal axis C. As a consequence, the electrode surface 42, or the opposing electrode surface, of the electrode 32 comes into contact with the blood vessel at the central part thereof in the direction along the longitudinal axis C. With the blood vessel being grasped between the grasping jaws 15 and 16, the surgeon performs a control input through the control button 18B. When the control input has been performed through the control button 18B, a high frequency electric current flows through the blood vessel across the electrode 32 of the first grasping jaw 15 and the second grasping jaw 16 and at the same time, the blood vessel is incised with frictional heat generated by the ultrasonic vibrations, as in the treatment of the incision of the liver parenchyma.

In the treatment upon each of the incision of the liver parenchyma and the incision of the liver blood vessel, a liquid such as physiological saline may be caused to flow from a liquid source 29 into the lumen 71 through the inside of the feed tube 23. In this case, the liquid flows out from the lumen 71, primarily through the opening of the clearance 72, toward the side toward which the first grasping jaw 15 is closed, in other words, the side of the grasping surface 35, and to the outside of the first grasping jaw 15. At this time, the liquid also flows out from the openings of the respective clearances 73, 75, and 76 toward the side toward which the first grasping jaw 15 is closed, although in a very small amount. The liquid which has flowed out from the opening of the clearance 72 sticks on the electrode surface 42 by surface tension. With the liquid being stuck on the electrode surface 42, the incision of the treatment object, specifically the liver parenchyma or liver blood vessel is performed, so that sticking of the treatment object to the electrode surface 42 is prevented and the char formation or the like of the treatment object is also reduced.

In this embodiment, the liquid which has flowed into the lumen 71 flows out toward the side toward which the first grasping jaw 15 is closed, in other words, the side of the grasping surface 35, to the outside of the first grasping jaw 15 only through the clearances 72, 73, 75, and 76 between the outer edges 47, 48, 51, and 52 of the electrode 32, or the electrode surface 42, and the recessed surface 43. Through the electrode 32, no hole or the like is formed extending from the electrode surface 42, or the opposing electrode surface, to the back electrode surface 46. Therefore, in the treatment upon each of the incision of the liver parenchyma and the incision of the liver blood vessel, a high frequency electric current uniformly flows through the entirety of the treatment object, specifically the liver parenchyma or liver blood vessel. As a consequence, stable treatment performance is maintained throughout the treatment upon each of the incision of the liver parenchyma and the incision of the liver blood vessel.

In the treatment upon each of the incision of the liver parenchyma and the incision of the liver blood vessel, heat generated at the heating element 22 may be used instead of ultrasonic vibrations. Described specifically, a control input is performed through the control button 18B, whereby high frequency electric energy is applied across the grasping jaws 15 and 16 from the energy control system 3 and at the same time, electric energy is supplied to the heating element 22 from the energy control system 3 so that heat is generated at the heating element 22.

Upon performing hemostasis in the liver, liver parenchyma is grasped between the grasping jaws 15 and 16 in the abdominal cavity or the grasping jaws 15 and 16 are brought into contact with the treatment object in the abdominal cavity with the grasping jaws 15 and 16 being kept open therebetween. Here, the grasping surface 35 of the first grasping jaw 15 and the grasping surface of the second grasping jaw 16, in other words, the surface of the second grasping jaw 16, the surface opposing the first grasping surface 15, are each normally brought into contact with the liver parenchyma only at the distal end portion thereof. In other words, the high frequency treatment instrument 2 comes into contact with the liver parenchyma at the distal end portions of the grasping jaws 15 and 16. Therefore, the electrode surface 42, or the opposing electrode surface, of the electrode 32 comes into contact with the liver parenchyma only at the distal end portion thereof, and is kept out of contact with the liver parenchyma at any part thereof other than the distal end portion. With the distal end portions of the respective grasping jaws 15 and 16 being kept in contact with the liver parenchyma, the surgeon performs a control input through the control button 18A, whereby high frequency electric energy is applied across the grasping jaws 15 and 16 from the energy control system 3 and at the same time, a high frequency electric current flows through the liver parenchyma, with which the grasping jaws 15 and 16 are kept in contact, and biological tissue such as blood vessels in the vicinity of the liver parenchyma across the electrode 32 of the first grasping jaw 15 and the second grasping jaw 16. As a consequence, proteins are denatured in the liver parenchyma, with which the grasping jaws 15 and 16 are kept in contact, and the biological tissue such as the blood vessels in the vicinity of the liver parenchyma, so that hemostasis, or coagulation, occurs in and around the liver parenchyma with which the grasping jaws 15 and 16 are kept in contact.

In the treatment of hemostasis in the liver, a liquid such as physiological saline is caused to flow from the liquid source 29 into the lumen 71 through the inside or the like of the feed tube 23, for example, before a high frequency electric current is caused to flow or at the same time as a high frequency electric current is caused to flow. As a consequence, a large majority of the liquid which has flowed into the lumen 71 flows out through the opening of the clearance 72, toward the side toward which the first grasping jaw 15 is closed, or the side of the grasping surface 35, and to the outside of the first grasping jaw 15. The clearance 72 is formed between the distal end electrode edge 47, or the distal end electrode surface, of the electrode 32 and the distal end wall 53, and is formed in the distal end portion of the first grasping jaw 15. Therefore, a large majority of the liquid which has flowed into the lumen 71 is caused to flow out, or ejected, toward the side toward which the first grasping jaw 15 is closed, at the distal end portion of the first grasping jaw 15. In the treatment of hemostasis in the liver, the distal end portion of the grasping surface 35 of the first grasping jaw 15 and the distal end portion of the second grasping jaw 16 come into contact with the treatment object as described hereinbefore. As the liquid flows out from the opening of the clearance 72, a large majority of the liquid which has flowed into the lumen 71 is, therefore, caused to flow out to the outside of the first grasping jaw 15 through the clearance 72 in the vicinity of the treatment object, or the liver parenchyma, with which the grasping jaws 15 and 16 are kept in contact. By causing an adequate amount of the liquid to flow out toward the side toward which the first grasping jaw 15 is closed, in the vicinity of the treatment object with which the grasping jaws 15 and 16 are kept in contact, the sticking of the treatment object to the electrode surface 42 is prevented, and the char formation or the like of the treatment object is also prevented.

Because a majority of the liquid which has flowed into the lumen 71 is caused to flow out from the clearance 72 to the outside of the first grasping jaw 15, substantially none of the liquid flows out from the openings of the respective clearances 73, 75, and 76. Therefore, the liquid which has been supplied to the lumen 71 is effectively prevented from flowing to any unintended part such as a part remote from the treatment object with which the distal end portion of the grasping surface 35 of the first grasping jaw 15 and the distal end portion of the second grasping jaw 16 are kept in contact. As a consequence, a high frequency electric current is effectively prevented from flowing through the liquid to biological tissue or the like other than the treatment object at a part remote from the treatment object, or the liver parenchyma. Hence, a high frequency electric current is efficiently applied to the treatment object with which the distal end portion of the grasping surface 35 of the first grasping jaw 15 and the distal end portion of the second grasping jaw 16 are kept in contact, so that hemostasis, or coagulation, in the liver is appropriately performed using the high frequency electric current.

Figure 5:
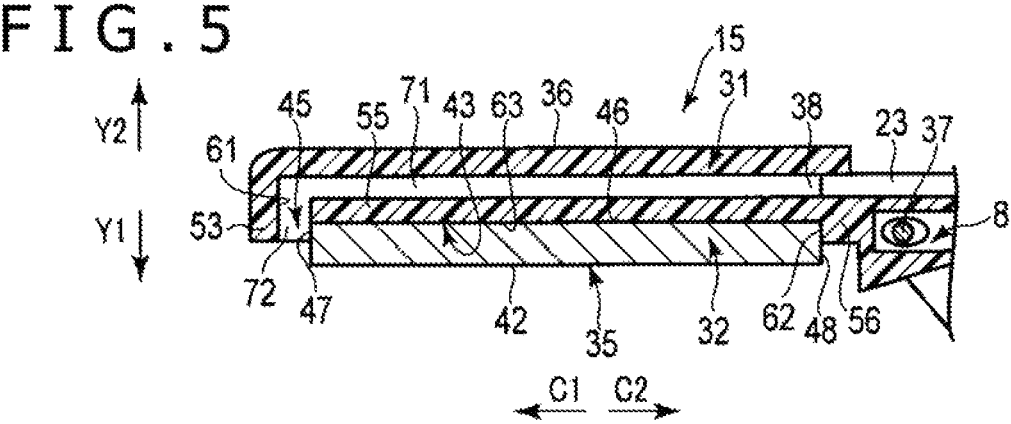
FIG. 5 is a cross-sectional view schematically depicting a first grasping jaw in a first modification in a cross-section substantially perpendicular to a width direction.
Figure 6:
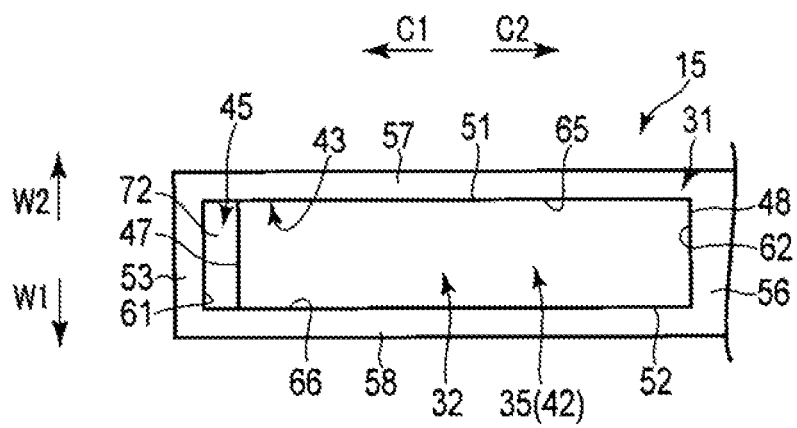
FIG. 6 is a schematic view of the first grasping jaw in the first modification as seen from a side toward which the first grasping jaw is closed.
Figure 7:
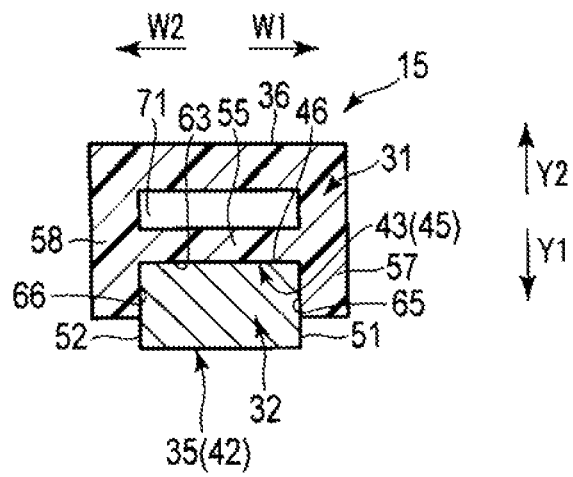
FIG. 7 is a cross-sectional view schematically depicting the first grasping jaw in the first modification in a cross-section substantially perpendicular to a direction along a longitudinal axis.

Modifications:

In the first embodiment, the electrode 32 is rockable relative to the support member 31, in other words, the first grasping jaw 15 is a so-called seesaw jaw or wiper jaw, but is not limited to such a grasping jaw. In a first modification depicted in FIGS. 5 to 7, an electrode 32 is fixed relative to a support member 31, and no pad member 33 is disposed. Also, in this modification, the support member 31 includes a recessed surface 43, and the electrode 32 is inserted in a recess 45, or a space, formed by the recessed surface 43. In this modification, however, a back electrode surface 46 is fixed on a recessed bottom surface 63 of a back wall 55, and the back electrode surface 46 is in contact with a recessed bottom surface 63. Similarly, a proximal end electrode edge 48 is in contact with a recessed proximal end surface 62 of a proximal end wall 56. Therefore, no clearance 73 is formed between the proximal end electrode edge 48 and the recessed proximal end surface 62. In this modification, a first side electrode surface 51 is in contact with a first recessed side surface 65 of a first side wall 57, and a second side electrode surface 52 is in contact with a second recessed side surface 66 of a second side wall 58. Therefore, no clearance 75 is formed between the first side electrode surface 51 and the first recessed side surface 65, and no clearance 76 is formed between the second side electrode surface 52 and the second recessed side surface 66.

In this modification, a lumen 71 is also disposed extending from the proximal end side to the distal end side inside the back wall 55. Also, in this modification, however, the lumen 71 is disposed extending toward the distal end portion of the first grasping jaw 15 inside the first grasping jaw 15. Further, the electrode 32 is disposed on the side toward which the first grasping jaw 15 is closed, in other words, the side of a grasping surface 35, with respect to the lumen 71. Also, in this modification, the lumen 71 communicates to the port 38, so that the liquid, which has been supplied toward the distal end side along the feed route or the like inside the feed tuber 23, flows from the port 38 into the lumen 71.

Also in this modification, between the distal end electrode edge 47, or the distal end electrode surface, of the electrode 32 and the recessed distal end surface 61 of the recessed surface 43, in other words, the distal end wall 53 of the support member 31, a clearance 72 is formed by the recess 45, or the space. The clearance 72 opens toward the side toward which the first grasping jaw 15 is closed, between the distal end electrode edge 47 of the electrode 32 and the distal end wall 53. In the first grasping jaw 15, the clearance 72 communicates to the lumen 71.

As described hereinbefore, none of the clearances 73, 75, and 76 is included in this modification. Also in this modification, the electrode 32 does not include any hole or the like that extends through the electrode 32 from the electrode surface 42, or the opposing electrode surface, to the back electrode surface 46, and the liquid which has flowed into the lumen 71 does not outwardly flow toward the side toward which the first grasping jaw 15 is closed, through the inside of the electrode 32. Therefore, a large majority of the liquid which has flowed into the lumen 71 flows into the clearance 72, and flows out from the opening of the clearance 72 toward the side toward which the first grasping jaw 15 is closed, or the side of the second grasping jaw 16, to the outside of the first grasping jaw 15. In other words, also in this modification, a large majority of the liquid which has flowed into the lumen 71 is caused to flow out, or ejected, toward the side toward which the first grasping jaw 15 is closed, at the distal end portion of the first grasping jaw 15. This modification, therefore, exhibits similar functions and advantageous effects as in the first embodiment.

In certain modifications, in the configuration that the electrode 32 is fixed relative to the support member 31 as in the first modification, the lumen 71 may be formed between the back electrode surface 46 of the electrode 32 and the recessed bottom surface 63 of the back wall 55 of the support member 31, as in the first embodiment. In these modifications, similar to the first modification, the proximal end electrode edge 48 is in contact with the recessed proximal end surface 62 of the proximal end wall 56 so that no clearance 73 is formed between the proximal end electrode edge 48 and the recessed proximal end surface 62. Further, the first side electrode surface 51 is in contact with the first recessed side surface 65 of the first side wall 57, and the second side electrode surface 52 is in contact with the second recessed side surface 66 of the second side wall 58. Therefore, similar to the first modification, no clearance 75 is formed between the first side electrode surface 51 and the first recessed side surface 65, and no clearance 76 is formed between the second side electrode surface 52 and the second recessed side surface 66.

Figure 8:
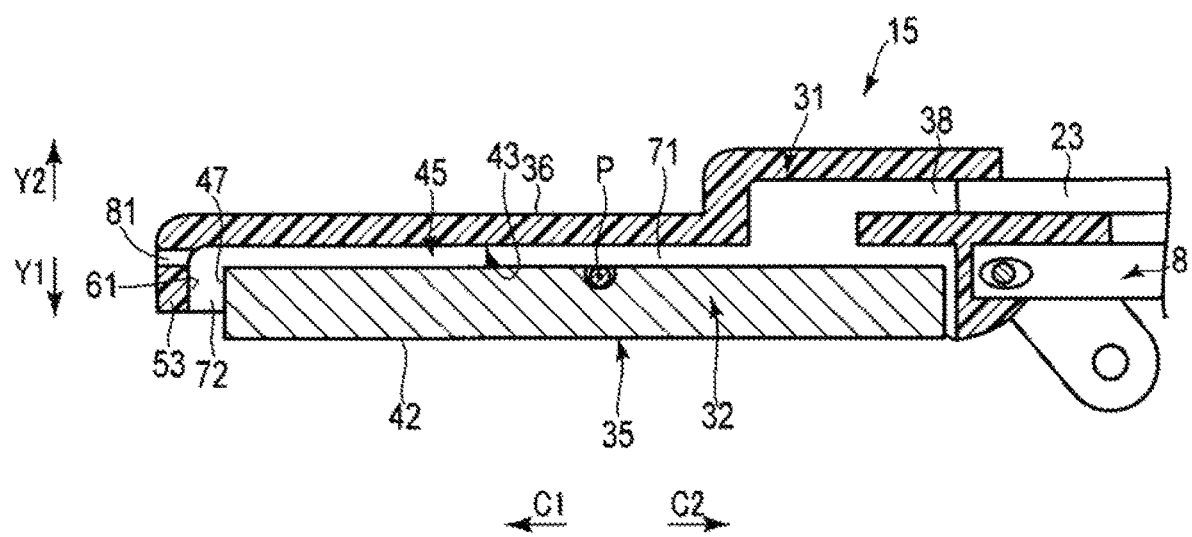
FIG. 8 is a cross-sectional view schematically depicting a first grasping jaw in a second modification in a cross-section substantially perpendicular to a width direction.
Figure 9:
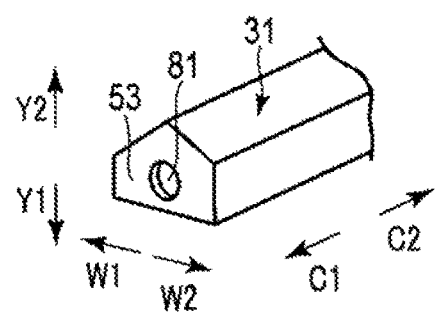
FIG. 9 is a perspective view schematically depicting a distal end portion of a support member in the first grasping jaw in the second modification.

In a second modification depicted in FIGS. 8 and 9, a through-hole 81 is formed in the support member 31 so that the through-hole 81 extends from the proximal end side toward the distal end side through the distal end wall 53. The though-hole 81 communicates to the lumen 71, and continues to the distal end side of the lumen 71. The through-hole 81 opens toward the distal end side in the outer surface of the first grasping jaw 15, in other words, the outer surface of the distal end wall 53.

This modification also exhibits similar functions and advantageous effects as in the first embodiment. In this modification, even if biological tissue, blood and the like flow in through the clearance 72 toward the lumen 71, the flowed-in biological tissue and the like are discharged together with the liquid from the opening of the through-hole 81 to the outside of the first grasping jaw 15. Further, after the end effector 7 has been pulled out of the body cavity, or abdominal cavity, an auxiliary tool (not depicted) can be inserted from the through-hole 81 into the clearance 72 and lumen 71, and the biological tissue and the like flowed into the clearance 72 can be removed using the auxiliary tool. Furthermore, after the end effector 7 has been pulled out of the body cavity, or abdominal cavity, a suction tube (not depicted) can be connected to the support member 31 via the through-hole 81, and a suction pressure can then be applied to the lumen 71 and clearance 72 to suck and recover the biological tissue and the like, which have flowed into the clearance 72, through the inside of the suction tube.

In the embodiment and modifications described hereinbefore, the first grasping jaw 15 of the high frequency treatment instrument 2 has the proximal end and the distal end, and in the first grasping jaw 15, the lumen 71 is internally formed toward the distal end portion. The high frequency treatment instrument 2 is openable and closeable between the first grasping jaw 15 and the second grasping jaw 16. The first grasping jaw 15 includes an electrode 32 on the side toward which the first grasping jaw 15 is closed, in other words, the side indicated by arrow Y1, with respect to the lumen 71. The electrode 32 has the electrode surface 42 arranged extending opposite the second grasping jaw 16 from the proximal end portion to the distal end portion of the first grasping jaw 15. In the first grasping jaw 15, the distal end wall 53 is disposed opposite the distal end edge 47 of the electrode surface 42 on the distal end side of the electrode 32, in other words, the side indicated by arrow C1, and between the distal end edge 47 of the electrode surface 42 and the distal end wall 53, the clearance 72 is formed in communication with the lumen 71. The clearance 72 opens toward the side toward which the first grasping jaw 15 is closed, in other words, the side indicated by arrow Y1, between the distal end edge 47 of the electrode surface 42 and the distal end wall 53.

In sum, a high frequency treatment instrument comprises a first grasping jaw having opposed respective proximal and distal end portions. The first grasping jaw includes a lumen formed therein that extends from the proximal end portion to the distal end portion. A second grasping jaw is configured to be engaged with the first grasping jaw so as to relatively pivot with respect to one another. The first grasping jaw includes an electrode coupled and extends over from the proximal end portion to the distal end portion of the first grasping jaw. The electrode is positioned to face against the second grasping jaw when the first grasping jaw and the second grasping jaw are in a closed position with respect to one another. The electrode has a distal end edge adjacent the distal end portion. The first grasping jaw forms a first clearance defined by a distal end wall positioned opposite the distal end edge of the electrode. The first clearance is in fluid communication with the lumen. The first grasping jaw includes a fluid port being connected to a fluid feed line to transfer fluid to the lumen.

The first grasping jaw includes a recessed surface recessed toward a side which the first grasping jaw is opened and the recessed surface containing the electrode therein. The distal end wall forms a distal end of the recessed surface and the fluid which has flowed into the lumen is directed to flow out toward the side which the first grasping jaw is closed through between an outer edge of the electrode and the recessed surface including the first clearance between the distal end wall and the distal end edge of the electrode. A distance between the distal end edge of the electrode and the distal end wall is greater than a distance between other part of the outer edge of the electrode other than the distal end edge and the recessed surface.

The high frequency treatment instrument further comprises a movable member connected to the first grasping jaw and configured to be drivable to open or to close the first grasping member with respect to the second grasping jaw. The first grasping jaw includes a support member having the distal end wall formed thereon and supports the electrode rockably. The high frequency treatment instrument further comprises an ultrasonic transducer that generates ultrasonic vibrations and transmits the generated ultrasonic vibrations to the second grasping jaw so as to cause the second grasping jaw being vibrated. At least one of the first grasping jaw and the second grasping jaw includes a heating element that generates heat. The first grasping jaw includes a recessed surface recessed toward a side toward which the first grasping jaw is opened. The recessed surface contains the electrode therein. The distal end wall forms a distal end of the recessed surface. The recessed surface and the electrodes form the first clearance and a second clearance therebetween and the fluid that flows into the lumen is directed to flow out toward the side which the first grasping jaw is closed, through the first clearance and the second clearance.

The disclosed technology is directed to a method of using a high frequency treatment instrument for treating liver parenchyma or a liver blood vessel. The method comprises the steps of grasping the liver parenchyma or liver blood vessel by respective first and second grasping jaws simultaneously in an abdominal cavity, causing a high frequency electric current to flow across an electrode. The electrode that is disposed between the respective first and second grasping jaws applies the high frequency electric current to the liver parenchyma or liver blood vessel. Next, directing a fluid into a lumen disposed in the first grasping jaw, before or during the application of the high frequency electric current to the liver parenchyma or liver blood vessel. And then, removing the fluid out from a clearance formed between a distal end edge of the electrode and a distal end wall disposed opposite the distal end edge of the electrode on the first grasping jaw.

A further aspect of the disclosed technology is directed to a treatment system comprises an energy control system. A high frequency treatment instrument is configured to be coupled to the energy control system so as to apply a high frequency electric current to a body tissue without sticking and/or char formation thereto. The high frequency treatment instrument comprises a housing having a handle attached thereto. A sheath has respective proximal and distal ends. The sheath is attached to the housing via the proximal end. An end effector is configured to be attached to the sheath via the distal end. The end effector includes respective first and second grasping jaws each of which is pivotally attached to the sheath. The first grasping jaw and/or second grasping jaw are capable of grasping the body tissue via the handle. The first grasping jaw includes an electrode being disposed in an inner side of the first grasping jaw to form a lumen therebetween. The lumen receives fluid from a fluid feed line so as to cool off the respective first and second grasping jaws during an operation and preventing char formation or sticking of the body tissue to the respective first and second grasping jaws. The first grasping jaw includes a recess formed in the inner side thereof to contain the electrode therein. The sheath includes a moveable member disposed therein and connected to the handle so as to permit the respective first and second grasping jaws pivoting with respect to one another. The first grasping jaw includes a support member formed thereon and being used to support the electrode rockably. At least one of the first grasping jaw and the second grasping jaw includes a heating element that generates heat.

The embodiment, examples and modifications of the present disclosure have been described hereinbefore. However, the present disclosure should not be limited to the embodiment described hereinbefore, examples and modifications, and various modifications are obviously feasible without departing from the spirit of the present disclosure.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A high frequency treatment instrument comprising:
a first grasping jaw extending along a longitudinal axis from a proximal end portion to a distal end portion, the first grasping jaw including a lumen formed therein that extends from the proximal end portion to the distal end portion; and
a second grasping jaw configured to be engaged with the first grasping jaw such that the first grasping jaw and the second grasping jaw are capable of relatively pivoting with respect to one another;
wherein the first grasping jaw includes an electrode that is coupled to the first grasping jaw and extends from the proximal end portion to the distal end portion of the first grasping jaw, the electrode being positioned to face against the second grasping jaw when the first grasping jaw and the second grasping jaw are in a closed position with respect to one another, the electrode including a distal end edge adjacent to the distal end portion, the distal end edge facing in a distal direction along the longitudinal axis of the first grasping jaw, the electrode including a proximal end edge adjacent to the proximal end portion, the proximal end edge facing in a proximal direction along the longitudinal axis of the first grasping jaw, the electrode including a side surface extending along the longitudinal axis of the first grasping jaw,
wherein the first grasping jaw further includes a support member having an electrically insulating property and supporting the electrode, the support member including a recess into which the electrode is inserted, the recess being formed by a distal end wall of the support member that is positioned on a distal side with respect to the distal end edge of the electrode, a proximal end wall of the support member positioned on a proximal side with respect to the proximal end edge of the electrode, a side wall of the support member opposed to the side surface of the electrode, and a recessed bottom surface of the support member opposed to a back surface of the electrode and forming the lumen,
wherein the first grasping jaw includes a fluid port that is connected to a fluid feed line and configured to transfer fluid to the lumen, and
wherein a distance between the distal end edge of the electrode and the distal end wall of the support member is larger than each of: (i) a distance between the proximal end edge of the electrode and the proximal end wall of the support member and (ii) a distance between the side surface of the electrode and the side wall of the support member.

2. The high frequency treatment instrument of claim 1, wherein
the recess is recessed in a direction away from the second grasping jaw, and
the lumen is configured to direct the fluid that flows therein to flow out in a direction toward a side of the second grasping jaw between an outer edge of the electrode and a surface of the recess including a first clearance formed between the distal end wall of the support member and the distal end edge of the electrode.

3. The high frequency treatment instrument of claim 1, further comprising: a movable member connected to the first grasping jaw and configured to be driven to open or to close the first grasping jaw with respect to the second grasping jaw.

4. The high frequency treatment instrument of claim 1, wherein the support member is configured to rockably support the electrode.

5. The high frequency treatment instrument of claim 1, further comprising: an ultrasonic transducer that is configured to generate ultrasonic vibrations and transmit the generated ultrasonic vibrations to the second grasping jaw so as to cause the second grasping jaw to be vibrated.

6. The high frequency treatment instrument of claim 1, wherein at least one of the first grasping jaw and the second grasping jaw includes a heating element that is configured to generate heat.

7. The high frequency treatment instrument of claim 1, wherein
the recess is recessed in a direction away from the second jaw, a first clearance and a second clearance are formed between a surface defining the recess and the electrode, and the lumen is configured to direct the fluid that flows therein to flow out in a direction toward a side of the second grasping jaw, through the first clearance and the second clearance.

8. The high frequency treatment instrument of claim 1, wherein the first grasping jaw forms a first clearance defined by the distal end wall of the support member and the distal end edge of the electrode along the longitudinal axis of the first grasping jaw, and the first clearance is in fluid communication with the lumen.

9. A treatment system comprising:
an energy control system; and
a high frequency treatment instrument configured to be coupled to the energy control system so as to apply a high frequency electric current to a body tissue without char formation and/or sticking thereto, the high frequency treatment instrument comprising
  a housing including a handle attached thereto,
  a sheath including a proximal end and a distal end, the sheath being attached to the housing via the proximal end, and
  an end effector configured to be attached to the sheath via the distal end, the end effector including a first grasping jaw and a second grasping jaw, each of which is pivotally attached to the sheath, the first grasping jaw and/or the second grasping jaw being capable of grasping the body tissue via the handle,
wherein the first grasping jaw extends along a longitudinal axis from a proximal end portion to a distal end portion and includes a lumen formed therein that extends from the proximal end portion to the distal end portion,
wherein the first grasping jaw includes an electrode that extends from the proximal end portion to the distal end portion of the first grasping jaw, the electrode including a distal end edge adjacent to the distal end portion of the first grasping jaw, the distal end edge facing in a distal direction along the longitudinal axis of the first grasping, the electrode including a proximal end edge adjacent to the proximal end portion, the proximal end edge facing in a proximal direction along the longitudinal axis of the first grasping jaw, the electrode including a side surface extending along the longitudinal axis of the first grasping jaw,
wherein the first grasping jaw further includes a support member having an electrically insulating property and supporting the electrode, the support member including a recess into which the electrode is inserted, the recess being formed by a distal end wall of the support member that is positioned on a distal side with respect to the distal end edge of the electrode, a proximal end wall of the support member positioned on a proximal side with respect to the proximal end edge of the electrode, a side wall of the support member opposed to the side surface of the electrode, and a recessed bottom surface of the support member opposed to a back surface of the electrode and forming the lumen, wherein the lumen is configured to receive fluid from a fluid feed line so as to cool off the first grasping jaw and the second grasping jaw during an operation and prevent char formation or sticking of the body tissue to the first grasping jaw and the second grasping jaw, and wherein a distance between the distal end edge of the electrode and the distal end wall of the support member is larger than each of: (i) a distance between the proximal end edge of the electrode and the proximal end wall of the support member and (ii) a distance between the side surface of the electrode and the side wall of the support member.

10. The treatment system of claim 9, wherein the sheath includes a moveable member disposed therein and connected to the handle so as to permit the first grasping jaw and the second grasping jaw to pivot with respect to one another.

11. The treatment system of claim 9, wherein the support member is configured to rockably support the electrode.

12. The treatment system of claim 9, wherein at least one of the first grasping jaw and the second grasping jaw includes a heating element that is configured to generate heat.

13. The high frequency treatment instrument of claim 1, wherein the electrode does not include a hole extending from an electrode surface in a direction towards the back surface formed on an opposite side of the electrode surface, the electrode surface facing towards the second grasping jaw.

14. The treatment system of claim 9, wherein the electrode does not include a hole extending from an electrode surface in a direction towards the back surface formed on an opposite side of the electrode surface, the electrode surface facing towards the second grasping jaw.

15. The treatment system of claim 9, wherein the first grasping jaw forms a first clearance defined by the distal end wall of the support member and the distal end edge of the electrode along the longitudinal axis of the first grasping jaw, and the first clearance is in fluid communication with the lumen.

* * * * *